United States Patent
Mabille et al.

(10) Patent No.: US 11,806,422 B2
(45) Date of Patent: Nov. 7, 2023

(54) HAIR REPAIR COMPOSITION (71) Applicant: RHODIA OPERATIONS, Paris (FR)

(72) Inventors: Caroline Mabille, Baron (FR); Katerina Karagianni, Paris (FR)

(*) Notice: Subject to any disclaimer, the term of this patent is extended or adjusted under 35 U.S.C. 154(b) by 0 days.

(21) Appl. No.: 16/611,400

(22) PCT Filed: May 4, 2018

(86) PCT No.: PCT/EP2018/061495
§ 371 (c)(1),
(2) Date: Nov. 6, 2019

(87) PCT Pub. No.: WO2018/206425
PCT Pub. Date: Nov. 15, 2018

(65) Prior Publication Data
US 2020/0163861 A1  May 28, 2020

(51) Int. Cl.
*A61K 8/73* (2006.01)
*A61Q 5/00* (2006.01)
*A61Q 5/06* (2006.01)

(52) U.S. Cl.
CPC ......... *A61K 8/737* (2013.01); *A61Q 5/002* (2013.01); *A61Q 5/004* (2013.01); *A61Q 5/06* (2013.01)

(58) Field of Classification Search
None
See application file for complete search history.

(56) References Cited

U.S. PATENT DOCUMENTS

| | | |
|---|---|---|
| 3,472,840 A | 10/1969 | Stone et al. |
| 4,031,307 A | 6/1977 | DeMartino et al. |
| 4,663,159 A | 5/1987 | Brode, II et al. |
| 4,959,464 A | 9/1990 | Yeh |
| 5,387,675 A | 2/1995 | Yeh |
| 5,473,059 A | 12/1995 | Yeh |
| 5,756,720 A | 5/1998 | Chowdhary |
| 6,258,348 B1 | 7/2001 | Tsivkin |
| 6,403,066 B1 | 6/2002 | Samain et al. |
| 2005/0089494 A1 | 4/2005 | Rigoletto, Jr. |
| 2006/0024260 A1 | 2/2006 | Bebot |

(Continued)

FOREIGN PATENT DOCUMENTS

| | | |
|---|---|---|
| EP | 1552807 A1 | 7/2005 |
| EP | 2425811 A1 | 3/2012 |

(Continued)

OTHER PUBLICATIONS

"International Cosmetic Ingredient Dictionary and Handbook", 2014, vol. 1, p. 1643, entry "Hydroxypropyl Guar Hydroxypropyltrimonium Chloride"; Personal Care Products Council—Washington, DC (USA).

(Continued)

*Primary Examiner* — Dominic Lazaro
(74) *Attorney, Agent, or Firm* — Jarrod N. Raphael (57) ABSTRACT

The invention relates to a method for mending split ends of hair comprising contacting the hair with split ends with a composition comprising at least cationic polygalactomannan containing non-ionic hydroxyalkyl substituents and having a Brookfield RVT viscosity at 25° C. and 20 rpm greater than 700 mPa·s, at a concentration of 1 pbw in water, for instance comprised between 700 and 1,200 mPa·s.

3 Claims, 3 Drawing Sheets

(56) References Cited

U.S. PATENT DOCUMENTS

| | | |
|---|---|---|
| 2006/0251603 A1 | 11/2006 | Rigoletto, Jr. et al. |
| 2009/0010855 A1 | 1/2009 | Lepilleur et al. |
| 2010/0029929 A1 | 2/2010 | Luczak et al. |
| 2010/0034765 A1 | 2/2010 | Herrwerth et al. |
| 2012/0021025 A1* | 1/2012 | Bendejacq ............. A61K 8/891 424/401 |
| 2012/0076747 A1 | 3/2012 | Bierganns et al. |
| 2014/0308227 A1* | 10/2014 | Mabille ................. A61K 8/922 424/70.13 |

FOREIGN PATENT DOCUMENTS

| | | |
|---|---|---|
| FR | 2709954 A1 | 3/1995 |
| FR | 2910308 A1 | 6/2008 |
| JP | 2001-526199 A | 12/2001 |
| JP | 2008-137990 A | 6/2008 |
| JP | 2011-528386 A | 11/2011 |
| JP | 2012-524038 A | 10/2012 |
| JP | 2016-532651 A | 10/2016 |
| WO | 99/32071 A2 | 7/1999 |
| WO | 2010/007040 A1 | 1/2010 |
| WO | 2010/118925 A2 | 10/2010 |
| WO | 2015/054026 A2 | 4/2015 |
| WO | 2016155932 A1 | 10/2016 |
| WO | 2018065418 A1 | 4/2018 |

OTHER PUBLICATIONS

Lamberti: "ESAFLOR HC 56 Technical Bulletin", Lamberti S.p.A. retrieved from the Internet: http://asia.in-cosmetics.com/_novadocuments/62371?v=635470640497630000 [retrieved on Jul. 6, 2017].

Ashland: "Techniques for Preparing Solutions of Cationic Guar", Announcement Ash, US, 2010, p. 1-6.

Anonymous: "Jaguar C-162 (Product data sheet E 90002010)", Rhodia, Sep. 2011 retrieved form the Internet: http://www.rhodia.com/product-literature-download.action?docId=090166368081a44b&doclanguage=. . . [retrieved on Jul. 6, 2017].

Anonymous: "Jaguar C-13S (Product data sheet N000717)", Rhodia, Sep. 2009 retrieved form the Internet: http://glenncorp.com/uploads/2013/07/Jaguar-C-13S-tds1.pdf [retrieved on Jul. 6, 2017].

Machine Translation of FR2709954.
Machine Translation of FR2910308.
Machine Translation of WO2016155932.

* cited by examiner

Percentage of the Initial Repair that is retained after N times shampoos:

Figure 4

HAIR REPAIR COMPOSITION

The present invention relates to a new cationic polygalactomannan containing non-ionic hydroxyalkyl substituents and having a specific viscosity.

The present invention relates also to hair care compositions for mending split ends, and more particularly to the use of a specific cationic polygalactomannan containing non-ionic hydroxyalkyl substituents and having a specific viscosity, as an agent for mending split ends.

Hair is a keratinous substance, which is repeatedly subjected to various stresses including especially environmental factors (such as exposure to UV radiation), damaging treatments (such as bleaching, coloring, perming or thermal straightening), and mechanical stressing, in particular during grooming procedures (for example by frequent brushing, back-combing or combing against high combing resistance).

It results in different types of structural damage to the hair: the cuticles are lifted, and the individual hair fibers may tend to become porous, to snarl, kink and/or interlock with each other.

Impact on the hair texture is noticeable for instance by a poor wet and dry combability, an increased electrostatic charge, increased brittleness, lack of manageability, reduced maximum tear force and elongation at break of the hair and/or split ends, so that the hair as a whole looks unhealthy (dull, lifeless, . . . ), is hard to comb and/or rough feel.

Among these damages, it is an object of the present invention to address the ever increasing demand in the market for hair care compositions which are useful for mending split ends.

The aim of the present invention is therefore to provide an ingredient which is useful for mending split ends.

"Split ends" refers to a condition wherein the ends of the hair are split into two or more shafts.

More especially it is defined as a longitudinal splitting of the hair fiber which develops after the protective cuticle has been stripped away from the end of the hair fibers as a result of either physical or chemical damaging of the hair. Split ends mainly form due to mechanical stresses during grooming routines and especially due to excessive combing forces.

Lubricating agents are already known to prevent or minimize formation of split ends. The lubrication reduces the friction in the hair during combing and hence reduces the strength of the abrasive forces to which the hair is being subjected. This in turn reduces the number of entanglements during the combing process.

The present invention, however, does not seek to prevent split ends damages.

The present invention is concerned with split ends mending, that is to say repair of existing damage by depositing substances that will restore axial cohesion to splits or "fill in" areas of shaft damage.

It is thus an object of the present invention to provide an ingredient which is effective in mending (i.e. repairing) split ends.

It is also an object of the present invention to provide an ingredient which is additionally effective in repairing hair cuticle damage and/or in aligning the hair fibers.

Repairing hair cuticle damage in the sense of the invention means smoothing hair cuticle. Visual effect may be observed for instance by looking at the hair fiber through scanning electron microscopy.

US 2005/0089494 and US 2006/0251603 disclose that the combination of polyquaternium-28 and methylvinylether/maleic acid copolymer, at particular ratios, produces a polyelectrolyte complex useful to repair split ends.

However, the stability of such polyelectrolyte complexes may be compromised when other ingredients are added to the hair care formulation. In particular, it has been reported that charged compounds and polymers could disrupt the structure of such polyelectrolyte complexes.

U.S. Pat. No. 6,258,348 discloses split-ends mending compositions comprising three polymers: guar, a betaine-based polyurethane surfactant, and a silicone polyurethane. As demonstrated in EP1552807 the amphoteric or cationic guar gums disclosed in U.S. Pat. No. 6,258,348 do not achieve substantial split ends repair in the absence of the other disclosed polymeric substituents.

The Applicant has now discovered unexpectedly that a specific cationic polygalactomannan containing non-ionic hydroxyalkyl substituents and having a specific viscosity is useful as an agent for mending split ends.

There has been no suggestion in the prior art that the specific cationic polygalactomannan containing non-ionic hydroxyalkyl substituents and having a specific viscosity as defined according to the present invention, used alone, would make it possible to achieve substantial split ends mending.

The subject of the invention is thus a cationic polygalactomannan containing non-ionic hydroxyalkyl substituents and having a Brookfield RVT viscosity at 25° C. and 20 rpm greater than 700 mPa·s, at a concentration of 1 pbw in water, for instance comprised between 700 and 1,200 mPa·s.

The present invention is also directed toward a personal care composition comprising at least one cationic polygalactomannan containing non-ionic hydroxyalkyl substituents and having a Brookfield RVT viscosity at 25° C. and 20 rpm greater than 700 mPa·s, at a concentration of 1 pbw in water, for instance comprised between 700 and 1,200 mPa·s.

The present invention also relates to a method for mending split ends of hair comprising contacting the hair with split ends with a composition comprising at least one cationic polygalactomannan containing non-ionic hydroxyalkyl substituents and having a Brookfield RVT viscosity at 25° C. and 20 rpm greater than 700 mPa·s, at a concentration of 1 pbw in water, for instance comprised between 700 and 1,200 mPa·s, as well as to the use of said cationic polygalactomannan containing non-ionic hydroxyalkyl substituents and having a specific viscosity as mentioned previously, as an agent for mending split ends.

It has been found that the specific cationic polygalactomannans containing non-ionic hydroxyalkyl substituents and having a specific viscosity according to the invention not only provide a high percentage of split ends mending, but are also able to close the split ends and to smooth the lifted cuticle scales so as to ensure a durable mend especially after combing or other stress factors during for example hair styling.

The specific cationic polygalactomannans containing non-ionic hydroxyalkyl substituents and having a specific viscosity according to the invention provide perceivable and durable split ends repair, from first use and onwards, after combing or washing.

From the first use of a composition containing the specific cationic polygalactomannans containing non-ionic hydroxyalkyl substituents and having a specific viscosity according to the invention, hair surface may advantageously look smoother, cuticles may partially be repaired and/or partial sealing of split ends may be achieved.

After several applications of a composition containing the specific cationic polygalactomannans containing non-ionic hydroxyalkyl substituents and having a specific viscosity according to the invention, split ends may advantageously be fully sealed and cuticles layed down.

These benefits can for instance be demonstrated through scanning electron microscopy, as shown in the Examples.

Advantageously, the specific cationic polygalactomannans containing non-ionic hydroxyalkyl substituents and having a specific viscosity according to the invention also provide split ends mending and hair cuticle repair, without dry hair negatives such as the greasy appearance or feel, sticky feel, loss of gloss and/or heavy, coated feel that many consumers experience when conventional cationic polymers with high charge density and high molecular weight are used.

Advantageously, no residual powder arises from the use of a specific cationic polygalactomannans containing non-ionic hydroxyalkyl substituents and having a specific viscosity according to the invention. This is advantageous compared for instance to the use of prior art polyelectrolyte complexes, which may result in significant residual white powder on hair that is visible to the naked eye.

A composition containing the specific cationic polygalactomannans containing non-ionic hydroxyalkyl substituents and having a specific viscosity according to the invention has a pleasant texture and spreadability, without stickiness on hands and hair.

Advantageously, the specific cationic polygalactomannans containing non-ionic hydroxyalkyl substituents and having a specific viscosity according to the invention also provide durable split ends repair, meaning in particular that split ends mending may resist several washing and/or combing cycles.

Advantageously, the cationic polygalactomannan containing non-ionic hydroxyalkyl substituents and having a specific viscosity according to the invention shows a surprising styling effect, typically curl retention of hair, when being applied on hair, regardless it is damaged or not.

According to a specific aspect, the present invention is directed towards the use of the cationic polygalactomannan as defined here-above as an agent for hair shaping, for example, for curl retention of hair.

Advantageously, when applied on hair after coloring process, the specific cationic polygalactomannan containing non-ionic hydroxyalkyl substituents and having a specific viscosity according to the invention may also provide durable color protection, meaning in particular that color application may resist several washing cycles.

According to another specific aspect, the present invention is directed towards the use of the cationic polygalactomannan as defined here-above as an agent for color protection.

Polygalactomannans

Galactomannans are polysaccharides consisting mainly of the monosaccharides mannose and galactose. The mannose-elements form a chain consisting of many hundreds of (1,4)-β-D-mannopyranosyl-residues, with 1,6 linked-D-galactopyranosyl-residues at varying distances, dependent on the plant of origin. Naturally occurring galactomannans are available from numerous sources, including guar gum, guar splits, locust bean gum, flame tree gum and cassia gum.

Additionally, galactomannans may also be obtained by classical synthetic routes or may be obtained by chemical modification of naturally occurring galactomannans.

Guar gum refers to the mucilage found in the seed of the leguminous plant *Cyamopsis tetragonolobus*. The water soluble fraction (85%) is called "guaran," which consists of linear chains of (1,4)-.β-D mannopyranosyl units-with α-D-galactopyranosyl units attached by (1,6) linkages. The ratio of D-galactose to D-mannose in guaran is about 1:2. Guar gum typically has a weight average molecular weight of between 2,000,000 and 5,000,000 g/mol. Guars having a reduced molecular weight, such as for example, from about 50,000 to about 2,000,000 g/mol are also known.

Guar seeds are composed of a pair of tough, non-brittle endosperm sections, hereafter referred to as "guar splits," between which is sandwiched the brittle embryo (germ). After dehulling, the seeds are split, the germ (43-47% of the seed) is removed by screening, and the splits are ground. The ground splits are reported to contain about 78-82% galactomannan polysaccharide and minor amounts of some proteinaceous material, inorganic non-surfactant salts, water-insoluble gum, and cell membranes, as well as some residual seedcoat and embryo.

Locust bean gum or carob bean gum is the refined endosperm of the seed of the carob tree, *Ceratonia siliqua*. The ratio of galactose to mannose for this type of gum is about 1:4. Locust bean gum is commercially available.

As mentioned previously, the polygalactomannan of the invention is a cationic polygalactomannan, that is to say a polygalactomannan that is substituted at one or more sites of the polygalactomannan with a substituent group that is a cationic substituent group.

The cationic polygalactomannan of the invention also contains non ionic hydroxyalkyl substituents. In other words, a cationic polygalactomannan of the invention is further substituted at one or more sites of the polygalactomannan with a substituent group that is a non ionic hydroxyalkyl substituent group. The hydroxyalkyl substituent group may be linear or branched, and may contain from 1 to 10 carbon atoms, especially from 1 to 5 carbon atoms, for instance from 2 to 4 carbon atoms. Mention may be made for instance of hydroxyethyl groups, hydroxypropyl groups and hydroxybutyl groups.

According to anyone of the invention embodiments, the polygalactomannan of the invention contains hydroxypropyl groups.

According to anyone of the invention embodiments, the galactomannan of the present invention is guar.

It may be for instance a cationic guar containing hydroxypropyl substituents, preferably a hydroxypropyl guar hydroxypropyltrimonium chloride.

The amount of cationic or of non ionic hydroxyalkyl substituents in a polygalactomannan of the invention may be characterized respectively by the degree of substitution or by the molar substitution of the polygalactomannan of the invention.

As used herein, the terminology "degree of substitution" in reference to a given type of derivatizing group and a given polygalactomannan means the number of the average number of such derivatizing groups attached to each monomeric unit of the polygalactomannan. In one embodiment, the derivatized polygalactomannan exhibits a total degree of substitution ("$DS_T$") of from about 0.001 to about 3.0, wherein:

$DS_T$ is the sum of the DS for cationic substituent groups ("$DS_{cationic}$") and the DS for nonionic substituent groups ("$DS_{nonionic}$"), $DS_{cationic}$ is from 0 to about 3, more typically from about 0.001 to about 2.0, and even more typically from about 0.001 to about 1.0, $DS_{nonionic}$ is from 0 to 3.0, more typically from about 0.001 to about 2.5, and even more typically from about 0.001 to about 1.0, and $DS_{cationic}$ and $DS_{nonionic}$, may be measured for instance by $^1$H-NMR.

As used herein, the term "molar substitution" or "ms" refers to the number of moles of derivatizing groups per moles of monosaccharide units of the guar. The molar substitution can be determined by the Zeisel-GC method. The molar substitution utilized by the present invention is typically in the range of from about 0.001 to about 3.

Processes for making polygalactomannans derivatives are known. In particular, processes for making derivatives of guar gum splits are generally known. Typically, guar splits are reacted with one or more derivatizing agents under appropriate reaction conditions to produce a guar polysaccharide having the desired substituent groups. Suitable derivatizing reagents are commercially available and typically contain a reactive functional group, such as an epoxy group, a chlorohydrin group, or an ethylenically unsaturated group, and at least one other substituent group, such as a cationic, nonionic or anionic substituent group, or a precursor of such a substituent group per molecule, wherein substituent group may be linked to the reactive functional group of the derivatizing agent by bivalent linking group, such as an alkylene or oxyalkylene group. Suitable cationic substituent groups include primary, secondary, or tertiary amino groups or quaternary ammonium, sulfonium, or phosphinium groups. Suitable nonionic substituent groups include hydroxyalkyl groups, such as hydroxypropyl groups. Suitable anionic groups include carboxyalkyl groups, such as carboxymethyl groups. The cationic, nonionic and/or anionic substituent groups may be introduced to the polysaccharide chains via a series of reactions or by simultaneous reactions with the respective appropriate derivatizing agents.

The polygalactomannans derivative, for instance the guar derivative, may be treated with a crosslinking agent, such as for example, borax (sodium tetra borate) is commonly used as a processing aid in the reaction step of the water-splits process to partially crosslink the surface of the guar splits and thereby reduces the amount of water absorbed by the guar splits during processing. Other crosslinkers, such as, for example, glyoxal or titanate compounds, are known.

After the preparation, the polygalactomannan of the invention can be treated with several known reagents, for example: caustic; acids; biochemical oxidants, such as galactose oxidase; chemical oxidants, such as hydrogen peroxide; and enzymatic reagents; or by physical methods using high speed agitation machines; thermal methods; and combinations of these reagents and methods. Reagents such as sodium metabisulfite or inorganic salts of bisulfite may also be optionally included.

The treatments described here above can be also performed on the polygalactomannan of the invention before the derivatization process.

In a preferred embodiment, the polygalactomannan is a depolymerized polygalactomannan, which has been depolymerized by using chemicals, such as hydrogen peroxide, or cellulase enzymes.

According to anyone of the invention embodiments, the polygalactomannan of the invention has a cationic degree of substitution DScat ranging from about 0.001 to about 3.

According to anyone of the invention embodiments, the polygalactomannan of the invention has a hydroxyalkyl molar substitution ranging from about 0.001 to about 3.

According to anyone of the invention embodiments, the polygalactomannan of the invention has a weight average molecular weight ranging from about 2,000 to about 5,000,000 g/mol.

The weight average molecular weight of a polygalactomannan of the invention may be measured for instance by SEC-MALS or by using gel permeation chromatography.

According to anyone of the invention embodiments, the polygalactomannan of the invention is a cationic guar derivative having a cationic degree of substitution DScat comprised between about 0.1 and about 1, a hydroxyalkyl molar substitution comprised between about 0.1 and about 1 and a weight average molecular weight comprised between about 500,000 g/mol and about 4,000,000 g/mol.

As an alternative to polygalactomannans, mention may be made of other polysaccharide polymers including, for example, chitosan, pectin, alginate, hyaluronic acid, agar, xanthan, dextrin, starch, cellulose, amylose, amylopectin, alternan, gellan, levan, mutan, dextran, pullulan, fructan, gum arabic, carrageenan, glycogen, glycosaminoglycans, murein, xyloglucans (such as tamarind gum and tamarind gum derivatives such as hydroxypropyl tamarind gum) and bacterial capsular polysaccharides.

Viscosity

It has been found unexpectedly that cationic polygalactomannan containing non-ionic hydroxyalkyl substituents as described previously, and having a specific viscosity, make it possible to achieve substantial split ends mending.

Specifically, it has been found that a hair care composition including a cationic polygalactomannan containing non-ionic hydroxyalkyl substituents and having a Brookfield RVT viscosity at 25° C. and 20 rpm greater than 700 mPa·s, at a concentration of 1 pbw in water, for instance comprised between 700 and 1,200 mPa·s, makes it possible to achieve improved split ends mending, relative to an otherwise identical hair care composition lacking a cationic polygalactomannan containing non-ionic hydroxyalkyl substituents as defined according to the invention.

It has also been found that a hair care composition including a cationic polygalactomannan containing non-ionic hydroxyalkyl substituents and having a Brookfield RVT viscosity at 25° C. and 20 rpm greater than 700 mPa·s, at a concentration of 1 pbw in water, for instance comprised between 700 and 1,200 mPa·s, makes it possible to achieve improved split ends mending, relative to an otherwise identical hair care composition including a cationic polygalactomannan containing non-ionic hydroxyalkyl substituents and having a Brookfield RVT viscosity at 25° C. and 20 rpm not in accordance with the invention.

Viscosity of the cationic polygalactomannan containing non-ionic hydroxyalkyl substituents of the invention is the viscosity in mPa·s measured using a Brookfield RVT viscosimeter using spindle 2 at 20 rpm in a water solution containing the cationic polygalactomannan containing non-ionic hydroxyalkyl substituents of the invention at a concentration of 1 pbw.

Rheological measurements may be performed for instance according to the following procedure:

weigh out 396 g of demineralised ultrapure water in a 600 ml beaker;

weigh out 4 g of a cationic polygalactomannan containing non-ionic hydroxyalkyl substituents of the invention and add it into the 600 ml beaker containing demineralised ultrapure water, under stirring;

keep stirring until a stable pH value is achieved and adjust pH to 5+/−0.1 with acetic acid;

measure viscosity of the resulting solution using a Brookfield RVT viscosimeter using spindle 2 at 20 rpm, after equilibration at 25° C. for 1 hour.

According to anyone of the invention embodiments, the cationic polygalactomannan containing non-ionic hydroxyalkyl substituents of the invention has a Brookfield RVT viscosity at 25° C. and 20 rpm comprised between 700 and 950 mPa·s, at a concentration of 1 pbw in water.

According to anyone of the invention embodiments, the cationic polygalactomannan containing non-ionic hydroxyalkyl substituents of the invention has a Brookfield RVT viscosity at 25° C. and 20 rpm comprised between 750 and 950 mPa·s, at a concentration of 1 pbw in water.

According to anyone of the invention embodiments, the cationic polygalactomannan containing non-ionic hydroxyalkyl substituents of the invention has a Brookfield RVT viscosity at 25° C. and 20 rpm comprised between 750 and 900 mPa·s, at a concentration of 1 pbw in water.

According to anyone of the invention embodiments, the cationic polygalactomannan containing non-ionic hydroxyalkyl substituents of the invention has a Brookfield RVT viscosity at 25° C. and 20 rpm comprised between 750 and 850 mPa·s, at a concentration of 1 pbw in water.

It is believed that high viscosities may negatively impact sensorial performance. For instance using a cationic polygalactomannan containing non-ionic hydroxyalkyl substituents and having a Brookfield RVT viscosity at 25° C. and 20 rpm greater than 1,200 mPa·s, for instance greater than 1,500 mPa·s, may be detrimental to the texture and/or spreadability of the formulation and/or may increase stickiness on hands and hair. Hair dry negatives such as the greasy appearance or feel, sticky feel, loss of gloss, heavy, coated feel and/or volume loss may also result from the use of such cationic polygalactomannans of higher viscosity.

A cationic polygalactomannan containing non-ionic hydroxyalkyl substituents and having a viscosity in accordance with the invention can be prepared by any suitable process known by the one skilled in the art. Methods for the preparation of polygalactomannan derivatives are disclosed for instance in U.S. Pat. Nos. 4,663,159; 5,473,059; 5,387,675; 3,472,840; 4,031,307; 4,959,464 and US 2010/0029929, all of which are incorporated herein by reference.

The composition of the invention may be a personal care composition, for instance a hair care composition.

In one embodiment, the subject of the invention is a hair care composition for mending split ends comprising at least one cationic polygalactomannan containing non-ionic hydroxyalkyl substituents and having a specific viscosity as defined previously, and being devoid of any other ingredient acting as split ends mending agent.

In other words, in one embodiment, a hair care composition for mending split ends of the invention comprises, as the sole agent for mending split ends, a cationic polygalactomannan containing non-ionic hydroxyalkyl substituents and having a specific viscosity as defined previously and contains no (0 pbw) other ingredient for that purpose.

Advantageously the specific cationic polygalactomannan containing non-ionic hydroxyalkyl substituents and having a specific viscosity according to the invention may be combined with a wide range of other hair benefit agents, including charged hair benefit agents. It is therefore possible to prepare hair care compositions for mending split ends including stable combinations of the specific cationic polygalactomannan containing non-ionic hydroxyalkyl substituents and having a specific viscosity according to the invention with other hair care ingredients that provide additional desirable properties.

Advantageously the specific cationic polygalactomannan containing non-ionic hydroxyalkyl substituents and having a specific viscosity according to the invention may be formulated in rinse-off or in leave-on hair care compositions. The performances in split ends mending are satisfactory in both formulations.

According to anyone of the invention embodiments, the hair care composition comprising a cationic polygalactomannan containing non-ionic hydroxyalkyl substituents and having a specific viscosity according to the invention may be formulated as rinse-off or leave-on type of products.

As used herein, the expression "rinse-off compositions" means compositions which are rinsed off from the hair after application. Reversely the expression "leave-on compositions" means compositions which are not rinsed off from the hair after application.

The non-limiting examples of rinse-off products include shampoos, conditioners, hair straighteners, permanent waves, and hair colors (encompassing permanent, semi-permanent, and temporary hair colors).

Leave-on type of hair care products include but not limited to the following representative examples such as setting lotions, serums, hair sprays, mousses, hair lacquers, hair gels, hair waxes, styling creams, pomades, and tonics. Mention is made that the term "hair spray," as used herein, refers to hair care products that are delivered in any atomized (spray) format, whether they be pressurized or unpressurized.

It is also considered to employ cationic polygalactomannan containing non-ionic hydroxyalkyl substituents and having a specific viscosity according to the invention in the following non-limiting type of hair care and/or hair styling based end-user formulations such as 2 in 1 shampoos, leave-on and rinse-off conditioners, hair perming products, hair relaxants, permanent hair dyeing systems, hair styling mousses, semi-permanent hair dyeing systems, temporary hair dyeing systems, hair bleaching agents, permanent hair wave systems, hair setting formulations, non-coloring hair preparations, hair-frizz-control gels, hair leave-in conditioners, hair de-tangling products, hair fixatives, hair conditioning mists, hair care pump sprays and other non-aerosol sprays, hair cuticle coats.

According to anyone of the invention embodiments, a composition of the invention contains from 0.01 to 10 pbw of a cationic polygalactomannan containing non-ionic hydroxyalkyl substituents and having a specific viscosity according to the invention, relative to the total weight of the composition, for instance from 0.05 to 5 pbw, for instance from 0.1 to 2 pbw.

The improved split ends mending achieved when using the cationic polygalactomannan containing non-ionic hydroxyalkyl substituents and having a specific viscosity according to the invention can be emphasized on communication tools used by suppliers of chemical ingredients of hair care compositions, for example on animations or movies, presentations, leaflets, flyers, posters, technical data sheets, formularies, on any support, including on papers and websites. This can be linked to a complete or semi complete composition, or to a particular ingredient used to prepare a composition. The improved split ends mending achieved when using the cationic polygalactomannan containing non-ionic hydroxyalkyl substituents and having a specific viscosity according to the invention can as well be emphasized on communication tools used in marketing hair care compositions, for example on commercial claims, labels, documentation linked to the composition, commercials, scientific studies backing commercial claims, on any support, including on papers, labels, websites, films or animation. Examples of commercial claims can include cure of split ends, deep repair of hair, split ends sealing or the like. Films or animation can for example show a hair fiber (or a representation thereof) having split ends and a product (or a representation thereof) approaching to the hair fiber and mending (i.e. repairing) split ends.

Some details or advantages of the invention will appear in the non-limitative examples below.

EXAMPLES

The invention will now be described in further detail by way of the following non limiting examples, wherein the abbreviations have the usual meaning in the art. Water amount indicated as "q.s." are intended to be "the amount required to complete to 100 pbw".

All ingredients are expressed by weight percent of the whole formulation and as level of active ingredients.

Example 1

The following serum compositions were prepared.

| | Control Formulation | Formulation of the invention | Comparative Formulation |
|---|---|---|---|
| Cationic polygalactomannan containing non-ionic hydroxyalkyl substituents of the invention[a] | — | 0.5 | — |
| Cationic polygalactomannan containing non-ionic hydroxyalkyl substituents, outside the scope of the invention[b] | — | — | 0.5 |
| Ethanol | 10 | 10 | 10 |
| Glycerin | 1 | 1 | 1 |
| Panthenol | 0.5 | 0.5 | 0.5 |
| Preservative | 0.5 | 0.5 | 0.5 |
| Water | q.s. | q.s. | q.s. |

[a]Hydroxypropyl Guar Hydroxypropyl trimonium chloride having a Brookfield RVT viscosity at 25° C. and 20 rpm comprised between 750 and 850 mPa.s, at a concentration of 1 pbw in water, available from Rhodia under the name Polycare Split Therapy
[b]Hydroxypropyl Guar Hydroxypropyl trimonium chloride having a Brookfield RVT viscosity at 25° C. and 20 rpm lower than 700 mPa.s, at a concentration of 1 pbw in water, available from Rhodia The polygalactomannans used in the formulation of the invention and in the comparative formulation have equivalent cationic degrees of substitution and hydroxyalkyl molar substitutions. They differ mainly from one another in terms of viscosity.

Formulation Procedure

Disperse the cationic polygalactomannan containing non-ionic hydroxyalkyl substituents in water. Add glycerin and panthenol. Adjust pH to 4.5-5. Add the preservative and adjust the pH to 4.7. Add the ethanol and verify the pH ($\leq$5). Add water to qsp 100.

Assessment of the Performances on Hair Tresses

Hair tresses were purchased from Kerling International European Natural Human Hair of the following characteristics: Color 5/0. 19 cm total length, 17 cm of free hair. 2.5 cm width. 4 g weight free hair.

Hair Pre-Treatment Protocol

Wet the tress during 1 min under running water (or soak during 10 min in water if using several hair tresses). Apply on the whole tress 3 ml of a 10 pbw active sodium diethoxylated dodecyl sulfate (SLE2S) solution. Shampoo during 1 min, 30 sec on each side. Rinse during 1 min. Squeeze between index and middle finger. Detangle using middle teeth comb followed by fine teeth comb. Leave overnight in the controlled climate room (RH=50%±10, T=23° C.)

Hair Damaging Protocol to Obtain Split Ends

The repeated grooming apparatus, custom-built, is used. The device consists of 10 compartments and allows 10 hair tresses to be combed simultaneously. The 4 combs per compartment are mounted at 90° angles, allowing one complete revolution to comb the tress 3 times. Collection drawers are located under each tress to collect the broken fragments. All experiments were performed under controlled temperature and humidity conditions, in a climate controlled room (RH=50%±10, T=23° C.).

The pre-treated hair tresses undergo repeated grooming during 7.5 hours at 19 rpm in order to create the split-ends

Measurement of the Percentage of Split Ends Repaired

The whole procedure takes place in the controlled climate room (RH=50%±10, T=23° C.). Use 4 g hair tresses pre-treated and then damaged according to the protocols described above. Pick 10 hair fibers all bearing split ends and glue them together with a scotch tape in order to obtain a 10-fiber kit. Count the split ends under the lighted magnifier. Weight 2 mg of the product (resp.: Control Formulation, Formulation of the invention or Comparative Formulation) in a plastic weighting cup with the aid of a 0.5 ml capacity disposable transfer pipette dropper, on high precision balance. Gather the 10 fibers by holding them close to the split ends and soak them in the product to collect the maximum quantity. Spread the product out on the split ends (on the approximately last 1 cm towards the tips) with the finger until product absorption. Smooth the fibers once more and put the 10-fiber kit in the oven during 1 min. If needed smooth once to align the fibers and count the split ends left under the lighted magnifier.

The percent of split ends repaired (% of Repair) was calculated as follows:

$$\% \text{ of Repair} = \frac{(\text{Original number of split ends}) - (\text{number of split ends left})}{\text{Original number of split ends}}$$

Results were the following:

| Formulation | Control Formulation | Formulation of the invention | Comparative Formulation |
|---|---|---|---|
| % of Repair (calculation) | 10 | 93 | 67 |
| % of Repair (trend) | Reference | +++ | + |

The formulation of the invention, which includes a specific cationic polygalactomannan containing non-ionic hydroxyalkyl substituents in accordance with the invention, exhibits significantly improved split ends mending compared to the Comparative Formulation (which includes a cationic polygalactomannan containing non-ionic hydroxyalkyl substituents outside the scope of the invention in terms of viscosity) and also compared to the Control Formulation (which contains no ingredient acting specifically as agent for mending split ends).

As evidenced by microscopy (Scanning Electron Microscopy), hair repair is perceivable.

Hair fibers that have been treated with the formulation of the invention look healthier from the first use and onwards.

Figure 1A:
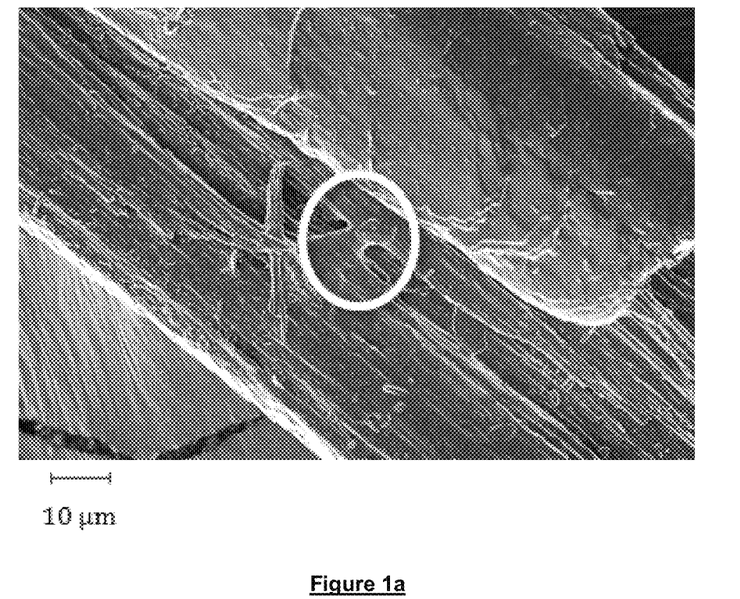
FIG. 1 shows the surface of hair after one (1) application of the formulation of the invention.
Figure 1B:
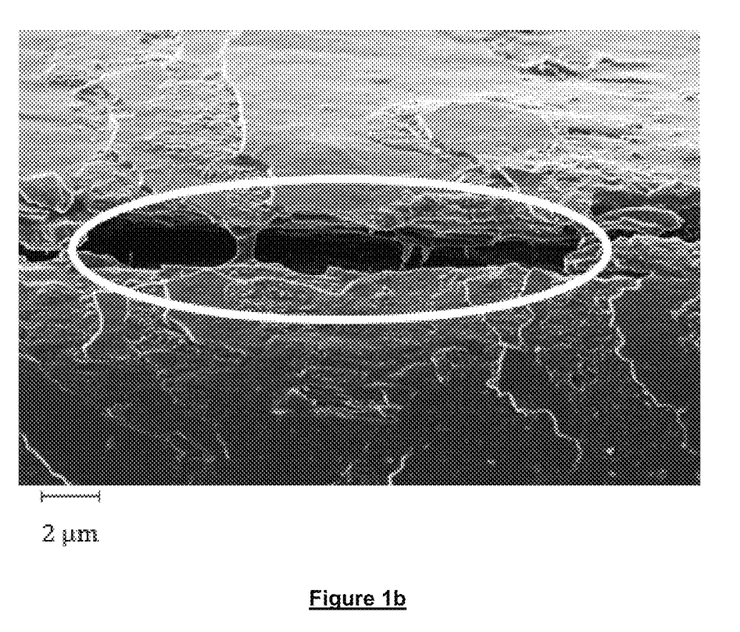

As depicted in FIG. 1, after 1 application of the formulation of the invention, hair surface looks smoother, cuticles are partially repaired and bridges are formed between the split ends (partial sealing of split ends is achieved, which is sufficient to bring the splits together). Hair ends diameter appears thicker and looks healthier.

Figures 2, 2A, 2B:
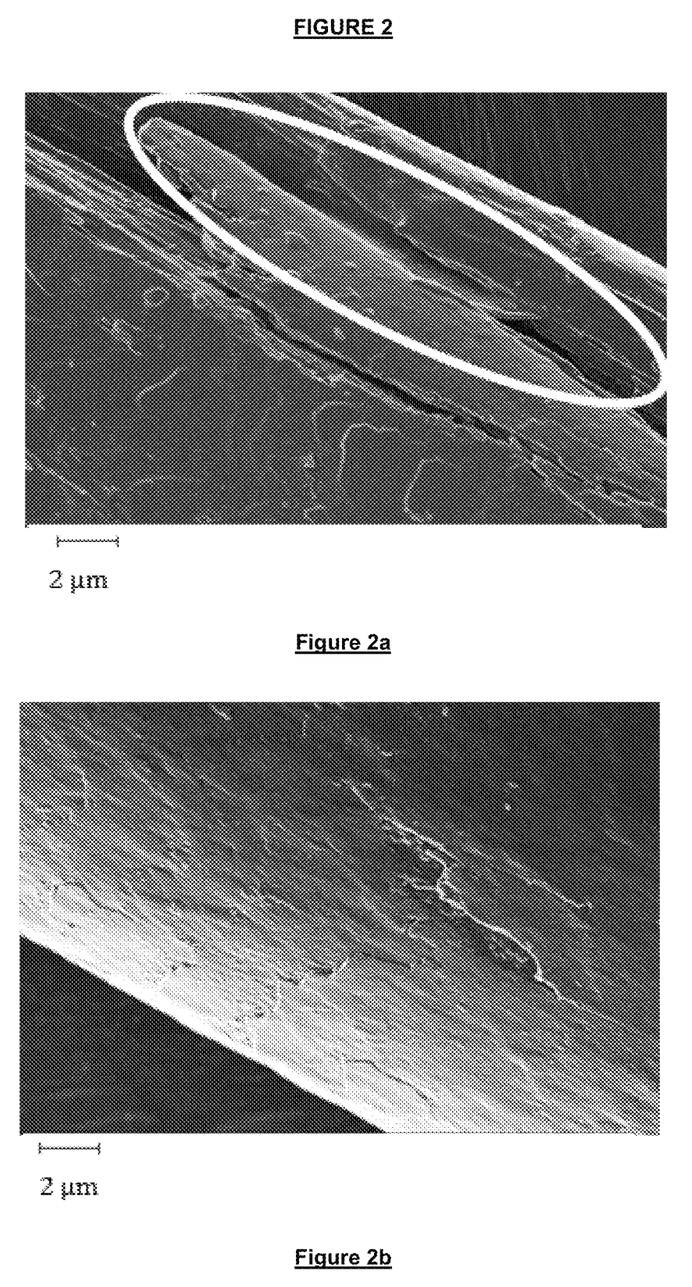
FIG. 2 shows split ends after three (3) consecutive applications of the formulation of the invention.

As depicted in FIG. 2, after several (3) consecutive applications of the formulation of the invention, split ends are fully sealed and cuticles layed down.

These examples illustrate that the specific cationic polygalactomannan containing non-ionic hydroxyalkyl substituents according to the invention, namely cationic polygalactomannan containing non-ionic hydroxyalkyl substituents having a Brookfield RVT viscosity at 25° C. and 20 rpm comprised between 700 and 1,200 mPa·s (and preferably lower than 950 mPa·s especially lower than 850 mPa·s), at a concentration of 1 pbw in water, is highly effective in mending split ends.

Example 2

The performances of a formulation in accordance with the invention have also been compared to a benchmark composition (namely TRESemmé Split Remedy Split Ends, which includes, as agent for mending split ends, a polyelectrolyte complex as taught in US 2005/0089494 and US 2006/0251603).

The following serum composition was prepared.

| | Formulation of the invention |
|---|---|
| Hydroxypropyl Guar Hydroxypropyl trimonium chloride having a Brookfield RVT viscosity at 25° C. and 20 rpm comprised between 750 and 850 mPa.s, at a concentration of 1 pbw in water[a] | 0.5 |
| Ethanol | 10 |
| Glycerin | 1 |
| Panthenol | 0.5 |
| Preservative | <0.5 |
| Water | q.s. |

[a] available from Rhodia under the name Polycare ® Split Therapy

The percentage of split ends repaired was measured following the same procedure and method as disclosed in Example 1.

Results were the following:

| Formulation | Control Formulation | Formulation of the invention | Benchmark formulation (TRESemmé Split Remedy Split Ends) |
|---|---|---|---|
| % of Repair (calculation) | 10 | 93 | 60 |
| % of Repair (trend) | Reference | +++ | + |

A formulation of the invention, which includes a specific cationic polygalactomannan containing non-ionic hydroxyalkyl substituents in accordance with the invention, exhibits significantly improved split ends mending compared to the benchmark formulation (which includes, as agent for mending split ends, a polyelectrolyte complex combining polyquaternium-28 and methylvinylether/maleic acid copolymer, at particular ratios) and compared to the Control Formulation (which contains no ingredient acting specifically as agent for mending split ends).

Tests also confirmed that split ends mending achieved when using the formulation of the invention resisted daily combing (everyday grooming).

Compared to this benchmark formulation, the formulation of the invention is easier to use (more versatile).

Sensory assessment also demonstrated that the formulation of the invention exhibited improved sensorial performance compared to this benchmark formulation.

Example 3

A "curl retention" test was set-up. The test takes place in a controlled climatic room (RH=50%±10, T=23° C.). Pre-treated bleached tresses of 4 grams are used. One tress is used per system.

Formulations

"Control Formulation" and "Formulation of the invention" as described in Example 1 are used. Hair tresses were purchased from Kerling International. European Natural Human Hair strong bleached, of the following characteristics: Color 10/0, 19 cm total length, 17 cm of free hair. 2.5 cm width. 4 g weight free hair.

Hair Pre-Treatment Protocol

Wet the tress during 1 min under running water (or soak during 10 min in water if using several hair tresses). Apply on the whole tress 3 ml of a 10 pbw active sodium diethoxylated dodecyl sulfate (SLE2S) solution. Shampoo during 1 min, 30 sec on each side. Rinse during 1 min. Squeeze between index and middle finger. Detangle using middle teeth comb followed by fine teeth comb. Leave overnight in the controlled climate room (RH=50%±10, T=23° C.)

Test Protocol To Evaluate The Curl Retention Attribute

1. Comb the tress twice with large teeth comb then twice with fine teeth comb.
2. Place the tresses on a mount with a grid background and take a picture of the initial appearance.
3. Apply 500 mg of the formulation on the last 5 cm of the tress: hold the tress at the tips by tightening the fibers then soak tips vertically in the formulation and massage the tips. Hold the tress at the mid-height and retrieve the remaining formulation of the container by scrubbing the tress on it. Massage during 30 s from top to bottom.
4. Gently wrap the tress around a curler.
5. Dry 20 min at 60° C., in a ventilated oven.
6. Gently remove the curler from the tress.
7. Place the tresses on the mount and take a picture at t=0.
8. Take pictures at 3 hours then at 72 hours.

Figure 3:
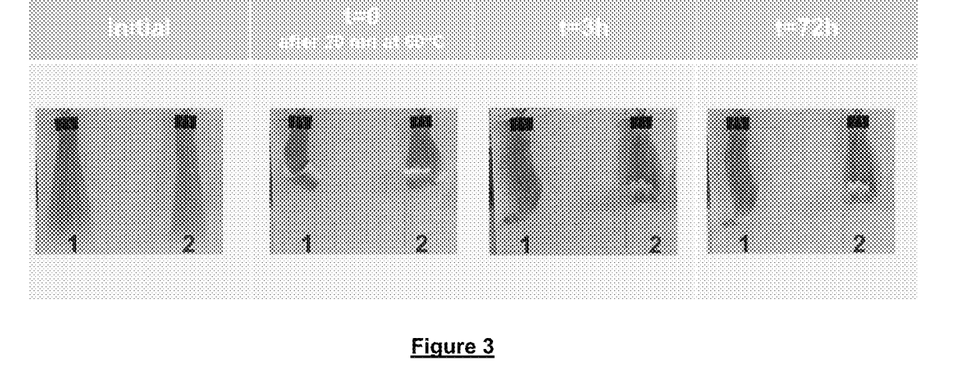
FIG. 3 shows the curl retention of tresses after treatment with a control formulation and a formulation of the invention.

Tress 1 was treated with the "Control Formulation" while Tress 2 was treated with the "Formulation of the invention" (FIG. 3).

As depicted in FIG. 3, the curl unties after 3 hours when treated with the "Control Formulation" (tress 1). The curl/shape is maintained even after 72 hours under the study conditions, when treated with the "Formulation of the invention" (tress 2).

The Formulation of the invention shows a good effect for shaping the hair, namely curl retention.

Example 4

In order to verify the durability of the Repair effect against washing, one application of the formulation was followed by several shampoo (washing) steps. At each step, the % Repair was evaluated. 5 hair tresses were used per system.

Formulations

The "Formulation of the invention" as described in Example 1 was used.

The (neutral) shampoo formulation was as follows: SLES (sodium lauryl ether sulfate) 12% wt CAPB (cocamidopropyl betaine) 2% wt, pH=5.

Hair tresses were purchased from Kerling International. European natural Human Hair of the following characteristics: Color 6/0, 20 cm total length, 18 cm of free hair. 2 g weight free hair.

The hair tresses were pre-treated (see Hair pre-treatment protocol). Then the hair tresses were altered by mechanical action using the apparatus Spin Split Hair®.

Each tress to be studied is attached to the apparatus and then subjected to the alternating brushing of the two brushes, while a hairdryer sends hot air continuously on the tress. The combined action of repeated brushing and heat contributes to the deterioration of the tress, and in particular to the production of split ends.

The tress is attached to the Spin Split Hair®. The unit is set at 75 rotations per minute. Each tress is subjected to an alteration cycle of one hour, which is equivalent to about 9000 strokes of brushes.

The tresses of hair are examined with a magnifying glass and tweezers. Each tress of hair is divided into 6 parts (subgroups) in which 50 hair fibers are selected and for each fiber, the technician identifies the presence or absence of a split end. For a tress, the technician raises a number of split ends per subgroup of tress, 6 values per tress and finally 30 values for all 5 tresses used per product. In the end, 1500 hair fibers are examined on all 5 tresses. The repair effect of the formulation was evaluated after the formulation application (Initial Repair) and after consecutive 1, 3, 5, and 10 shampoo applications.

Application rules:
Wet the tress and massage the whole length for 45 seconds with the neutral shampoo using 0.2 g of shampoo for 2 g of tress.
Rinse thoroughly for 45 seconds and squeeze between index and middle finger. Let air dry the tress. Count the initial number of split ends.
Apply 0.3 g of formulation (for 2 g tress) containing the Polycare® Split Therapy on the last 8 cm of the tress (tips).
Distribute the product on the tress by massaging.
Let air dry the tress. Count the number of split ends. This gives access to the Initial Repair. Then proceed to additional shampooing (as described above) with intermediate counts of the split ends after 1 shampoo, 3 shampoos, 5 shampoos and 10 shampoos. This gives access to the % of the Initial Repair that is retained after each shampooing (FIG. 4).

Figure 4:
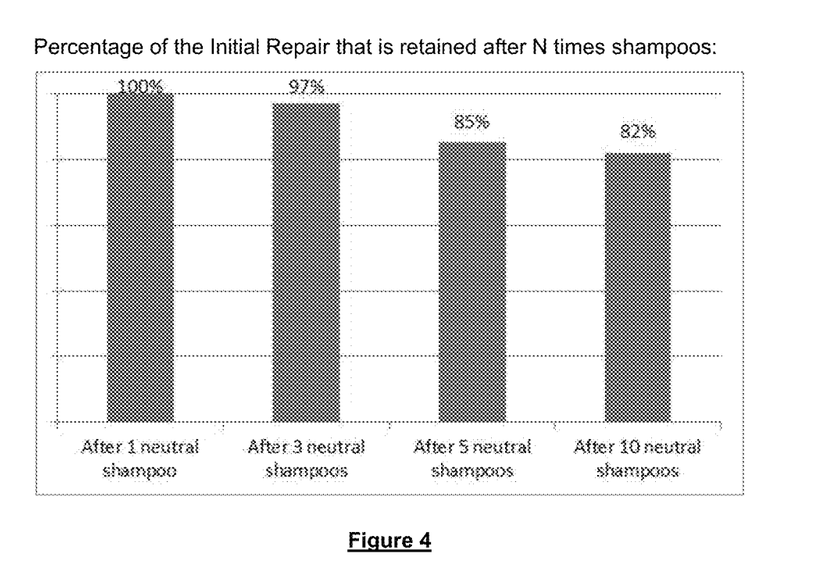
FIG. 4 shows the percentage of retained initial repair after one (1), three (3), five (5), and ten (10) neutral shampoo applications.

As depicted in FIG. 4, the performance is stable after 10 neutral shampoo applications: most of the repair obtained after 1 serum application is retained.

Thus the Repair effect of Formulation of the invention is durable against several washing cycles.

Example 5

Same formulation and tress alteration protocol as described above are used.

In order to verify the durability of the Repair effect against combing, one application of the formulation was followed by 20 combings. The % Repair was calculated. 5 hair tresses were used per system.

Application rules:
Wet the tress and massage the whole length for 45 seconds with the neutral shampoo using 0.2 g of shampoo for 2 g of tress.
Rinse thoroughly for 45 seconds and squeeze between index and middle finger. Let air dry the tress. Count the initial number of split ends.
Apply 0.3 g of formulation (for 2 g tress) containing the Polycare® Split Therapy on the last 8 cm of the tress (tips).
Distribute the product on the tress by massaging.
Let air dry the tress. Count the number of split ends. This gives access to the Initial Repair. Then proceed to 20 combings with a fine teeth comb. Count the number of split ends. This gives access to the % of the Initial Repair that is retained after 20 combings.

The test showed a 77% of the Initial Repair that is retained after 20 combings.

Thus the Repair effect of the Formulation of the invention is durable against several combings, which simulates the everyday grooming process of the consumers.

The invention claimed is:
1. A method for mending split ends of hair comprising contacting the hair with split ends with a composition comprising at least one cationic polygalactomannan having non-ionic hydroxyalkyl substituents and the cationic poly- galactomannan having a Brookfield RVT viscosity at 25° C. and 20 rpm of greater than 700 mPa·s, at a concentration of 1 pbw in water, wherein the cationic polygalactomannan is the only component for mending split ends in the composition.

2. A method for maintaining curl retention of hair comprising contacting the hair with a composition comprising at least one cationic polygalactomannan having nonionic hydroxyalkyl substituents and the cationic polygalactomannan having a Brookfield RVT viscosity at 25° C. and 20 rpm of greater than 700 mPa·s, at a concentration of 1 pbw in water, wherein the cationic polygalactomannan is the only component for maintaining curl retention of hair in the composition.

3. A method for protecting hair color comprising contacting the hair with a composition comprising at least one cationic polygalactomannan having non-ionic hydroxyalkyl substituents and the cationic polygalactomannan having a Brookfield RVT viscosity at 25° C. and 20 rpm of greater than 700 mPa·s, at a concentration of 1 pbw in water, wherein the cationic-polygalactomannan is the only component for protecting hair color in the composition.

\* \* \* \* \*

UNITED STATES PATENT AND TRADEMARK OFFICE
CERTIFICATE OF CORRECTION

PATENT NO. : 11,806,422 B2
APPLICATION NO. : 16/611400
DATED : November 7, 2023
INVENTOR(S) : Caroline Mabille and Katerina Karagianni Page 1 of 1

It is certified that error appears in the above-identified patent and that said Letters Patent is hereby corrected as shown below:

On the Title Page

A Foreign Application Priority Data item (30) should be added as follows:
(30) Foreign Application Priority Data
May 10, 2017 (EP) .......................................... 17170371

Signed and Sealed this
Twentieth Day of February, 2024

Katherine Kelly Vidal
*Director of the United States Patent and Trademark Office*